(12) United States Patent
Tuszynski et al.

(10) Patent No.: US 6,451,306 B1
(45) Date of Patent: *Sep. 17, 2002

(54) METHODS FOR THERAPY OF NEURODEGENERATIVE DISEASE OF THE BRAIN

(75) Inventors: Mark H. Tuszynski; Fred Gage, both of La Jolla, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/060,543

(22) Filed: Apr. 15, 1998

(51) Int. Cl.[7] .................. A01N 63/00; A01N 43/04; C12N 15/00; C12N 15/63
(52) U.S. Cl. .................. 424/93.21; 424/93.2; 514/44; 435/320.1; 435/455
(58) Field of Search ............... 514/44; 424/93.2, 424/93.21; 435/172.1, 455, 320.1

(56) References Cited

U.S. PATENT DOCUMENTS 5,650,148 A * 7/1997 Gage et al. ............. 424/93.2
5,762,926 A * 6/1998 Gage et al. ............. 424/93.21

FOREIGN PATENT DOCUMENTS

WO       WO 90/06757      * 6/1990

OTHER PUBLICATIONS

Blesch et al., Clinical Neuroscience, vol. 3, p. 268–274, 1996.*
Yang et al., Journal of Neurotrauma, vol. 14(5), p. 281–297, May 1997.*

* cited by examiner

Primary Examiner—Scott D. Priebe
Assistant Examiner—Shin-Lin Chen
(74) Attorney, Agent, or Firm—Foley & Lardner

(57) ABSTRACT

The invention provides a specific protocol for use in grafting donor cells genetically modified to produce nerve growth factors into grafting sites within the cholinergic basal forebrain and is especially useful in treating neurodegenerative conditions such as Alzheimer's Disease. Grafting sites are selected for proximity to previously identified defective, diseased or damaged brain cells. Each graft is situated no more than about 550 $\mu$m from a targeted cell and no more than about 5 mm from another graft. Depending on the size of the region to be treated, the number of grafting sites will vary upwards of 10 sites, with between 5 and 10 sites serving to deliver a therapeutically significant dosage of nerve growth factors to targeted cells. Donor cells are delivered in a composition concentration of at least $1 \times 10^5$ cells/$\mu$l, wherein each graft is comprised of between 2 and 20 $\mu$l of the donor cell composition. The composition is delivered to each grafting site over a period of about 5–10 minutes.

12 Claims, No Drawings

METHODS FOR THERAPY OF NEURODEGENERATIVE DISEASE OF THE BRAIN

FIELD OF THE INVENTION

The invention relates to methods for treatment of neurodegenerative disease and methods for delivery of neurotrophic factors into the mammalian brain.

HISTORY OF THE RELATED ART

Neurotrophic factors play a physiological role in the development and regulation of neurons in mammals. In adults, basal forebrain cholinergic neurons, motor neurons and sensory neurons of the CNS retain responsiveness to neurotrophic factors and can regenerate after loss or damage in their presence. For this reason, neurotrophins are considered to have great promise as drugs for the treatment of neurodegenerative conditions such as Alzheimer's Disease (AD), Parkinson's Disease (PD), amyotrophic lateral sclerosis (ALS), peripheral sensory neuropathies and spinal cord injuries.

Clinical trials for the use of neurotrophins in the treatment of AD, ALS and sensory neuropathies are underway. However, the search for a protocol for delivery of neurotrophins to target tissues with minimal side effects (e. g., from diffusion to non-targeted cells or immune reaction to the delivery vehicle) and sufficient penetration of the CNS (e. g., bypassing the blood-brain barrier and achieving chronic delivery of neurotrophin to target cells) has not yet revealed a clear path for clinical administration of neurotrophins. In particular, effective delivery methods and dosing parameters have not yet been identified, although several methods have been proposed. Therefore, although the prospects for therapy of neurodegenerative disease of the brain and CNS are believed to be bright, a successful clinical protocol remains elusive.

SUMMARY OF THE INVENTION

The invention provides a protocol for delivery of recombinant nerve growth factors into the mammalian brain. The invention is particularly useful in treating neurodegenerative conditions in large primates, in whom nerve growth factors delivered according to the invention stimulate growth of neurons and recovery of function.

More specifically, the invention consists of methods for intraparencymal delivery of recombinant nerve growth factors to defective, diseased or damaged cells in the mammalian brain. In one aspect, the invention provides a specific protocol for use in grafting donor cells genetically modified to produce nerve growth factors into grafting sites within the cholinergic basal forebrain. Grafting sites are selected for proximity to previously identified defective, diseased or damaged brain cells. To intensify exposure of such cells to the delivered growth factors, each graft is situated no more than about 550 µm from a targeted cell and no more than about 5 mm from another graft. Depending on the size of the region to be treated, the number of grafting sites will vary upwards of 10 sites, with between 5 and 10 sites serving to deliver a therapeutically significant dosage of nerve growth factors to targeted cells.

For most clinical applications, donor cells will be delivered as part of a pharmaceutically acceptable composition. Each composition contains a concentration of donor cells of at least $1\times10^5$ cells/µl. Each graft is comprised of between 2 and 20 µl of a donor cell composition. The composition is delivered to each grafting site in the target tissue through a surgical incision over a period of about 5–10 minutes (depending on the total volume of cell suspension to be delivered). The rate of delivery of the cells may therefore vary from about 0.2 µl cell suspension/minute to about 4 µl cell suspension/minute.

Particularly useful nerve growth factors for use in the invention are the neurotrophins. Of the neurotrophins, particularly useful compounds are β-NGF (beta nerve growth factor) and NT3 (neurotrophin 3). The brain is an immune-protected environment; however, use of species-matched nerve growth factor encoding transgenes will reduce the risk of an unforseen adverse immune reaction to the transgene product.

This targeted, regionally specific protocol for neurotrophin delivery avoids limitations imposed by diffusion of substances across the blood-brain barrier and through central nervous system (CNS) parenchyma, while avoiding adverse effects of neurotrophic factors delivered intact in a non-directed manner to the CNS.

DETAILED DESCRIPTION OF THE INVENTION

I. Target Tissue and Dosing Parameters for Use in Practicing the Invention

The invention identifies two parameters required for successful regeneration of neurons in the brain with neurotrophic factors; especially, the neurons whose loss is associated with neurodegenerative conditions with impairment of cognition such as Alzheimer's Diesease (AD).

The first parameter defined by the invention is the target tissue. A region of the brain is selected for its retained responsiveness to neurotrophins. In humans, CNS neurons which retain responsiveness to neurotrophins into adulthood include the cholinergic basal forebrain neurons, the entorhinal corical neurons, the thalamic neurons, the locus ceruleus neurons, the spinal sensory neurons and the spinal motor neurons. For treatment of neurodegenerative conditions with impairment of cognition such as AD, the preferred target tissue is the Ch4 region of the basal forebrain.

Magnocellular neurons Ch1–Ch4 of the primate basal forebrain provide cholinergic innervation to the cerebral cortex, thalamus and basolateral nucleus of amygdala. In subjects with neurodegenerative diseases such as AD, neurons in the Ch4 region (nucleus basalis of Meynert) which have nerve growth factor (NGF) receptors undergo marked atrophy as compared to normal controls (see, e. g., Kobayashi, et al., *Mol. Chem. Neuropathol.*, 15:193–206 (1991); Higgins and Mufson, *Exp. Neurol.*, 106:222–236 (1989); Mufson, et aL, *Exp. Neurol*, 105:221–232 (1989) and, Mufson and Kordower, *Prog. Clin. Biol. Res.*, 317:401–414 (1989)). In normal subjects, NGF prevents sympathetic and sensory neuronal death during development and prevents cholinergic neuronal degeneration in adult rats and primates (Tuszynski, et al., *Gene Therapy*, 3:305–314 (1996)). The resulting loss of functioning neurons in this region of the basal forebrain is believed to be causatively linked to the cognitive decline experienced by subjects suffering from neurodegenerative conditions such as AD (Tuszynski, et al., supra and, Lehericy, et al., *J Comp. Neurol.*, 330:15–31 (1993)).

For therapy of neurodegenerative disease in humans, an appropriate region of the basal forebrain is treated with a neurotrophic factor. Within the targeted region, a neurotrophic factor is preferably delivered into 5 to 10 separate sites, depending on the condition treated. For example, in human AD, basal forebrain neuronal loss occurs over an intraparenchymal area of approximately 1 cm in diameter. To treat affected neurons over such a large region, affixation of grafts at upwards of 10 separate sites is desirable. However, in treating localized injuries to the basal forebrain, the affected areas of the brain will likely be smaller such that selection of fewer grafting sites (e. g., 5 or fewer) will be sufficient for restoration of a clinically significant number of cholinergic neurons.

Importantly, specific grafting sites are selected so as to cluster in an area of neuronal loss. Such areas may be identified clinically using a number of known techniques, including magnetic resonance imaging (MRI) and biopsy. In humans, non-invasive, in vivo imaging methods such as MRI will be preferred. Once areas of neuronal loss are identified, grafting sites are selected for stereotaxic distribution so each graft is placed at a distance of no more than about 550 µm from an injured neuron and at a distance of 5 mm or less from another graft.

The second parameter defined by the invention is the dosage of neurotrophic factor to be delivered into the target tissue. In this regard, "dosage" refers to both concentration of neurotrophic factor encoding cells/graft and rate of delivery of the cells into the target tissue. total number of grafts made. As described in greater detail elsewhere below, grafts are placed by infusing the cell suspension through a surgical incision to the graft site.

For most clinical applications, donor cells will be delivered as part of a pharmaceutically acceptable composition (examples of which are provided elsewhere herein). Each composition contains a concentration of donor cells of at least $1 \times 10^5$ cells/µl. Each graft is comprised of between 2 and 20 µl of a donor cell composition. The composition is delivered to each grafting site in the target tissue through a surgical incision over a period of about 5–10 minutes (depending on the total volume of cell suspension to be delivered). The rate of delivery of the cells may therefore vary from about 0.2 µl cell suspension/minute to about 4 µl cell suspension/minute.

II. Materials for Use in Practicing the Invention

Materials useful in the methods of the invention include ex vivo compatible recombinant expression vectors, cells and cell lines, encapsulation materials, pharmaceutically acceptable carriers and polynucleotides coding for nerve growth factors of interest.

A. Neurotrophic Factors

Known nerve growth factors (NGFs) include a primary nerve growth factor (NGF), brain-derived neurotrophic factor (BDNF), neurotrophin 3 (NT3), neurotrophin 4/5 (NT-4/5), neurotrophin 6 (NT-6), ciliary neurotrophic factor (CNTF), glial cell line-derived neurotrophic factor (GDNF), fibroblast growth factor 2 (FGF-2), leukaemia inhibitory factor (LIF) and certain members of the insulin-like growth factor family (e. g., IGF-1). NGF and NT3 in particular have been tested with promising results in clinical trials and animal studies (see, e. g., Hefti and Weiner, *Ann Neurol.,* 20:275–281 (1986); Tuszynki and Gage, *Ann. Neurol.,* 30:625–636 (1991); Tuszynski, et al., Gene Therapy, 3:305–314 (1996) and Blesch and Tuszynski, *Clin. Neurosci.,* 3:268–274 (1996)). Of the known nerve growth factors, β NGF (for treatment of the Ch4, as in AD) and GNGF (for treatment of the substantia nigra, as in PD) are preferred for use in the invention.

Human (h) β NGF and hNT3 are preferred for use in therapy of human disease according to the invention due to their relatively low immunogenicity as compared to allogenic growth factors. However, other nerve growth factors are known which may also be suitable for use in the invention with adequate testing of the kind described herein.

Coding polynucleotides for hβ NGF and hNT3 are known, as are coding sequences for neurotrophins of other mammalian species (e. g., mouse, in which the coding sequence for β NGF is highly homologous to the human coding sequence). For example, a cDNA including the coding sequence for hβ NGF is reported in GenBank at E03015 (Kazuo, et al., Japanese Patent Application No. JP19911175976-A, while the nucleotide sequence of genomic β NGF (with putative amino acid sequence) is reported in GenBank at HSBNGF (Ullrich, *Nature,* 303:821–825 (1983)) and the mRNA sequence is reported in GenBank at HSBNGFAC (Borsani, et al., *Nucleic Acids Res.,* 18:4020 (1990)). The genomic nucleotide sequence of hNT3 is reported in GenBank at E07844 (Asae, et al., JP Patent Application No. 1993189770-A4). These references are incorporated herein to illustrate knowledge in the art concerning nucleotide and amino acid sequences for use in synthesis of neurotrophins. Exemplary nucleotide sequences coding for βNGF and NT3 can be obtained from the GENBANK nucleotide database Accession Nos. X52599 and E07844, respectively.

B. Donor Cells for Grafting

A preferred method for preparation of donor cells containing a nerve growth factor transgene encoding expression vector is described in detail in commonly assigned U.S. Pat. No. 5,650,148, the contents of which are incorporated herein. The preparation is carried out by modifying donor cells such as fibroblasts by introduction of a retroviral vector containing a transgene or transgenes encoding nerve growth factor (NGF) protein.

The strategy for transferring genes into donor cells in vitro includes the following basic steps: (1) selection of an appropriate transgene or transgenes whose expression is correlated with CNS disease or dysfunction; (2) selection and development of suitable and efficient vectors for gene transfer; (3) preparation of donor cells from primary cultures or from established cell lines; (4) demonstration that the donor implanted cells expressing the new function are viable and can express the transgene products(s) stably and efficiently; (5) demonstration that the transplantation causes no serious deleterious effects; and (6) demonstration of a desired phenotypic effect in the host animal.

The methods described below to modify donor cells using retroviral vectors and grafting into the CNS are merely for purposes of illustration and are typical of those that might be used. However, other procedures may also be employed, as is understood in the art. In particular, most of the techniques used to transform cells, construct vectors and the like are widely practiced in the art, and most practitioners are familiar with the standard resource materials which describe specific conditions and procedures. However, for convenience, the following paragraphs may serve as a useful guideline.

1. Choice of Donor Cells

The choice of donor cells for implantation depends heavily on the nature of the expressed gene, characteristics of the vector and the desired phenotypic result. Because retroviral vectors require cell division and DNA synthesis for efficient infection, integration and gene expression (Weiss et al., RNA *Tumor viruses*, 2nd Ed., Weiss et al., eds., Cold Spring Harbor Press, New York (1985)), if such vectors are used, the donor cells are preferably actively growing cells such as primary fibroblast culture or established cell lines, replicating embryonic neuronal cells or replicating adult neuronal cells from selected areas such as the olfactory mucosa and possibly developing or reactive glia. Primary cells, i. e. cells that have been freshly obtained from a subject, such as fibroblasts, that are not in the transformed state are preferred for use in the present invention. Other suitable donor cells include immortalized (transformed cells that continue to divide) fibroblasts, glial cells, adrenal cells, hippocampal cells, keratinocytes, hepatocytes, connective tissue cells, ependymal cells, bone marrow cells, stem cells, leukocytes, chromaffin cells and other mammalian cells susceptible to genetic manipulation and grafting using the methods of the present invention. Species-matched cells are preferred; e. g., primate cells for delivery to primates, human cells for delivery to humans and so forth.

The application of methods to induce a state of susceptibility in stationary, non-replicating target cells may make many other cell types suitable targets for viral transduction. For instance, methods have been developed that permit the successful retroviral vector infection of primary cultures of adult rat hepatocytes, ordinarily refractory to infection with such vectors, and similar methods may be helpful for a number of other cells (Wolff et al., *Proc. Natl. Acad. Sci. USA* 84:3344–3348 (1987)). In addition, the development of many other kinds of vectors derived from herpes, vaccinia, adenovirus, or other viruses, as well as the use of efficient non-viral methods for introducing DNA into donor cells such as electroporation (Toneguzzo et al., *Molec. Cell. Biol.* 6:703–706 (196)), lipofection or direct gene insertion may be used for gene transfer into many other cells presently not susceptible to retroviral vector infection.

Additional characteristics of donor cells which are relevant to successful grafting include the age of the donor cells. The results presented herein demonstrate that aged human cells may be used for transfection with transgenes for grafting.

2. Choice of Vector

Although other vectors may be used, preferred vectors for use in the methods of the present invention are viral, including retroviral, vectors. The viral vector selected should meet the following criteria: 1) the vector must be able to infect the donor cells and thus viral vectors having an appropriate host range must be selected; 2) the transferred gene should be capable of persisting and being expressed in a cell for an extended period of time without causing cell death for stable maintenance and expression in the cell; and 3) the vector should do little, if any, damage to target cells. Murine retroviral vectors offer an efficient, useful, and presently the best-characterized means of introducing and expressing foreign genes efficiently in mammalian cells. These vectors have very broad host and cell type ranges, integrate by reasonably well understood mechanisms into random sites in the host genome, express genes stably and efficiently, and under most conditions do not kill or obviously damage their host cells.

Examples of retroviral vectors in which a single transgene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple transgenes. All of these vectors can transfer or incorporate a gene for a selectable marker so that transduced cells can be identified and generated. Because its characteristics are well-known and it stably expresses transgene product, MoMuLV is an especially desirable vector for use in delivering nerve growth factors into the brain according to the invention.

Construction of vectors for recombinant expression of nerve growth factors for use in the invention may be accomplished using conventional techniques which do not require detailed explanation to one of ordinary skill in the art. For review, however, those of ordinary skill may wish to consult Maniatis et al., in *Molecular Cloning: A Laboratory Manual*, Cold Spring Harbor Laboratory, New York (1982).

Briefly, construction of recombinant expression vectors employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., (*Nucleic Acids Res.*, 9:309, 1981), the method of Maxam, et al., (*Methods in Enzymology*, 65:499, 1980), or other suitable methods which will be known to those skilled in the art. Size separation of cleaved fragments is performed using conventional gel electrophoresis as described, for example, by Maniatis, et al., (*Molecular Cloning*, pp. 133–134, 1982).

3. Transgene Transformation of Donor Cells

Host cells may be transformed with expression vectors and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

Functional DNA transgenes may be inserted into donor cells by means other than vectors. For example, non-vector methods include nonviral physical transfection of DNA into cells; for example, microinjection (DePamphilis et al., *BioTechnique* 6:662–680 (1988)); electroporation (Tonequzzo et al., *Molec. Cell. Biol.* 6:703–706 (1986), Potter, *Anal. Biochem.* 174:: 361–33 (1988)); chemically mediated transfection such as calcium phosphate transfection (Graham and van der EB, supra, Chen and Okayama, *Mol. Cell. Biol.* 7:2745–2752 (1987), Chen and Okayama, *BioTechnique*, 6:632–638 (1988)) and DEAE-dextran mediated transfer (McCutchan and Pagano, *J Natl. Cancer Inst.* 41:351–357 (1968)); cationic liposomal mediated transfection (Felgner et al., *Proc. Natl. Acad. Sci. USA*, 84:7413–7417 (1987), Felgner and Holm, Focus 11:21–25 (1989) and Felgner et al., *Proc. West. Pharmacol. Soc.* 32:115–121 (1989)) and other methods known in the art.

The donor cells must be properly prepared for grafting. For example, for injection of genetically modified donor cells according to the present invention, cells such as fibroblasts obtained from skin samples are placed in a suitable culture medium for growth and maintenance of the cells, for example a solution containing fetal calf serum (FCS) and allowed to grow to confluency. The cells are loosened from the culture substrate for example using a buffered solution such as phosphate buffered saline (PBS) containing 0.05% trypsin and placed in a buffered solution such as PBS supplemented with 1 mg/ml of glucose; 0.1 mg/ml of $MgCl_2$; 0.1 mg/ml $CaCl_2$ (complete PBS) plus 5% serum to inactivate trypsin. The cells may be washed with PBS using centrifugation and are then resuspended in the complete PBS without trypsin and at a selected density for injection. In addition to PBS, any osmotically balanced solution which is physiologically compatible with the host subject may be used to suspend and inject the donor cells into the host.

The long-term survival of implanted cells may depend on effects of the viral infection on the cells, on cellular damage produced by the culture conditions, on the mechanics of cell implantation, or the establishment of adequate vascularization, and on the immune response of the host animal to the foreign cells or to the introduced gene product. The mammalian brain has traditionally been considered to be an immunologically privileged organ, but recent work has shown conclusively that immune responses can be demonstrated to foreign antigens in the rat brain. It is important to minimize the potential for rejection and graft-versus-host reaction induced by the grafted cells by using autologous cells wherever feasible, by the use of vectors that will not produce changes in cell surface antigens other than those associated with the phenotypic correction and possibly by the introduction of the cells during a phase of immune tolerance of the host animal, as in fetal life.

Issues of appropriate or faithful gene expression must be resolved to ensure that the level of gene expression is sufficient to achieve the desired phenotypic effect and not so high as to be toxic to the cell.

A problem associated with the use of genetically engineered cells as transplants for gene therapy is that as cells become quiescent (non-dividing) the expression of genes, including transgenes, has been observed to decrease ("down regulate") (Palmer et al., *Proc. Natl. Acad. Sci. USA* 88:1330–334 (1991)). Primary fibroblasts grafted into the brain do not continue to divide when implanted unless they are transformed and tumorigenic. They thus exist in a quiescent state in the brain. It is thus useful to provide means for maintaining and/or increasing expression of the transgene in the absence of cell division to promote long term stable expression of therapeutic genes used in fibroblasts for gene therapy.

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., *Cell* 27:299 (1981); Corden et al., *Science* 209:1406 (1980); and Breathnach and Chambon, *Ann. Rev. Biochem.* 50:349 (1981)). For retroviruses, control elements involved int he replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, N.Y. (1982)). Malawian murine leukemia virus (MLV) and Rous sarcoma virus (RSV) LTRs contain promoter and enhancer sequences (Jolly et al., *Nucleic Acids Res.* 11:1855 (1983); Capecchi et al., In: Enhancer and eukaryotic gene expression., Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., *Nature* 314:285 (1985); Rossi and de Crombrugghe, *Proc. Natl. Acad. Sci. USA* 84:5590–5594 (1987)). Methods for maintaining and increasing expression of transgenes in quiescent cells include the use of promoters including collagen type I ($\alpha$1 and $\alpha$2) (Prockop and Kivirikko, *N. Eng. J Med.* 311:376 (1984); Smith and Niles, *Biochem.* 19:1820 (1980); de Wet et al., *J. Biol. Chem.*, 258:14385 (1983)), SV40 and LTR promoters.

In addition to using viral and non-viral promoters to drive transgene expression in donor cells such as primary fibroblasts, an enhancer sequence may be used to increase the level of transgene expression. Enhancers can increase the transcriptional activity not only of their native gene but also of some foreign genes (Armelor, *Proc. Natl. Acad. Sci. USA* 70:2702 (1973)). For example, in the present invention collagen enhancer sequences are used with the collagen promoter $\alpha 2(I)$ to increase transgene expression. In addition, the enhancer element found in SV40 viruses may be used to increase transgene expression. This enhancer sequence consists of a 72 base pair repeat as described by Gruss et al., *Proc. Natl. Acad. Sci. USA* 78: 943 (1981); Benoist and Chambon, *Nature* 290:304 (1981), and From and Berg, *J. Mol. Appl. Genetics,* 1:457 (1982), all of which are incorporated by reference herein. This repeat sequence can increase the transcription of many different viral and cellular genes when it is present in series with various promoters (Moreau et al., *Nucleic Acids Res.* 9:6047 (1981).

Transgene expression may also be increased for long term stable expression after grafting using cytokines to modulate promoter activity. Several cytokines have been reported to modulate the expression of transgene from collagen $\alpha 2(I)$ and LTR promoters (Chua et al., connective Tissue Res., 25:161–170 (1990); Elias et al., Annals N. Y. Acad. Sci., 580:233–244 (1990)); Seliger et al., J. Immunol. 141:2138–2144 (1988) and Seliger et al., J. Virology 62:619–621 (1988)). For example, transforming growth factor (TGF)$\beta$, interleukin (IL)-1$\beta$, and interferon (INF)$\alpha$ or $\gamma$ down regulate the expression of transgenes driven by various promoters such as LTR. Tumor necrosis factor (TNF)$\alpha$ and TGF$\beta$1 up regulate and IL1$\beta$, may be used to control expression of transgenes driven by a promoter in donor cells such as fibroblasts. Other cytokines that may prove useful include basic fibroblast growth factor (bFGF) and epidermal growth factor (EGF).

Collagen promoter with the collagen enhancer sequence (Coil(E)) can also be used to take advantage of the high level of cytokines present in the brain following grafting of the modified donor cells to increase transgene expression. In addition, anti-inflammatory agents including steroids, for example dexamethasone, may be administered to the graft recipient immediately after implantation of the fibroblasts and continued, preferably, until the cytokine-mediated inflammatory response subsides. In certain cases, an immunosuppression agent such as cyclosporin may be administered to reduce the production of interferon-$\gamma$ which downregulates LTR promoter and Coll(E) promoter-enhancer, and reduces transgene expression.

For in vivo use, transgenes driven by collagen promoter are introduced into cells and then directly implanted into the brain without requiring further intervention. The cytokines released after grafting as part of the recipient's natural response will stimulate the collagen promoter driven transcription of the selected transgene.

Cytokines including the growth factors bFGF and EGF, may also be administered before, during or after grafting, to promote survival of grafted donor ells in the CNS.

It is also useful to be able to regulate the secretion of the genetically engineered gene product after grafting. As shown in an embodiment presented herein, the release of a gene product such as acetylcholine (Ach), a transmitter, greatly decreased in Alzheimer's Disease, from cultured cells infected with a MLV vector expressing the choline acetyltransferase cDNA can be augmented using choline, a precursor for acetylcholine. This suggests a means for dietary regulation of intracerebral gene therapy.

Therefore, the phenotypic effects of fibroblast or other non-neuronal donor cells or target cells in vivo is believed to be through the diffusion of a required gene product or metabolite, through gap junctions or through uptake by target cells of secreted donor cell gene products or metabolites. The donor cell may also act as a toxin "sink" by expressing a new gene product and metabolizing and clearing a neurotoxin.

In primates, transduced primary primate fibroblasts have been shown to express human NGF in vivo in the brain and CNS for up to 12 months, thereby providing a chronically available source for local NGF delivery to these tissues according to the invention.

4. Pharmaceutical Preparations of Donor Cells

Compositions of neurotrophin encoding transgenes may be placed into a pharmaceutically acceptable suspension, solution or emulsion. Suitable mediums include saline and may, for those embodiments which do not rely on antigen presenting cells for delivery of the neurotrophin transgenes into target tissue, liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Further, a composition of neurotrophin transgenes may be lyophilized using means well known in the art, for subsequent reconstitution and use according to the invention.

In addition to the targeted vector delivery systems discussed supra, a colloidal dispersion system may also be used for targeted delivery. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of operatively encoding transgenes in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

III. Methods for Donor Cell Grafting Into Target Tissue

The most effective mode and timing of grafting of the transgene donor cells of the invention to treat defects, disease or trauma in the CNS of a patient will depend on the severity of the defect and on the severity and course of disease or injury to cells such as neurons in the CNS, the patient's health and response to treatment and the judgment of the treating health professional.

Neural transplantation or "grafting" involves transplantation of cells into the ventricular cavities or subdurally onto the surface of a host brain. Conditions for successful transplantation included: 1) viability of the implant; 2) retention of the graft at the site of transplantation; and 3) minimum amount of pathological reaction at the site of transplantation. Methods for transplanting various nerve tissues, for example embryonic brain tissue, into host brains have been described in Neural Grafting in the Mammalian CNS, Bjorklund and Stenevi, eds., (1985) Das. Ch. 3 pp. 23–30; Freed, Ch. 4, pp. 31–40; Stenevi et al., Ch. 5, pp. 41–50; Brundin et al., Ch.

6, pp. 51–60; David et al., Ch. 7, pp. 61–70; Seiger, Ch. 8, pp. 71–77 (1985), incorporated by reference herein. These procedures include intraparenchymal transplantation, i. e., within the host brain (as compared to outside the brain or extraparenchymal transplantation) achieved by injection or deposition of tissue within the host brain so as to be opposed to the brain parenchyma at the time of transplantation (Das, supra).

The two main procedures for intraparenchymal transplantation are: 1) injecting the donor cells within the host brain parenchyma or 2) preparing a cavity by surgical means to expose the host brain parenchyma and then depositing the graft into the cavity (Das, supra). Both methods provide parenchymal apposition between the graft and host brain tissue at the time of grafting, and both facilitate anatomical integration between the graft and host brain tissue. This is of importance if it is required that the graft become an integral part of the host brain and to survive for the life of the host.

IV. Animal Models and Clinical Evaluation

An animal model that mimics loss of cholinergic neurons in, for example, AD is transection of the fornix pathway connecting the septum from the hippocampus. Such transections cause retrograde degeneration of cholinergic and non-cholinergic cell bodies in the septal nucleus of rats and primates. Although accompanied by adverse side effects, the degeneration can be prevented in this model through pump infusion of neurotrophins into the brain, thus demonstrating the tractability of the model to treatment with neurotrophins.

Data demonstrating the use and efficacy of the methods of the invention in this animal model (derived from non-human primates to best approximate the size requirements of the primate brain) are provided in the Examples.

Clinical evaluation and monitoring of treatment can be performed using the in vivo imaging techniques described above as well as through biopsy and histological analysis of treated tissue. In the latter respsect, basal forebrain cholinergic neuronal numbers can be quantified in a tissue sample using, for example, anti-neurotrophin antibody (for immunoassay of secreted neurotrophin) or NGF-receptor (p75) and choline acetyltransferase (ChAT) for labeling of neurons. A sample protocol for in vitro histological analysis of treated and control tissue samples is described in the Examples.

The invention having been fully described, examples illustrating its practice are set forth below. These examples should not, however, be considered to limit the scope of the invention, which is defined by the appended claims.

In the examples, the abbreviation "min. " refers to minutes, "hrs" and "h" refer to hours, and measurement units (such as "ml") are referred to by standard abbreviations. All printed materials cited are incorporated herein by reference.

EXAMPLE I

Primate Animal Model of Diseased, Defective or Damaged Brain Cells

Twelve aged and four adult non-aged Macaca mulatta (rhesus) monkeys were experimental subjects. Non-aged animals (n=4, mean age=9.64±1.90 yrs) did not undergo surgical procedures and their intact brains were studied. Aged monkeys were divided into two experimental groups: NGF recipients (n=6, mean age=22.55±0.56 yrs) and control subjects (n=6, mean age=23.51±1.07 yrs). All procedures and animal care adhered strictly to NIH, AAALAC, USDA, Society for Neuroscience, and internal institutional guidelines for experimental animal health, safety and comfort.

EXAMPLE II

Preparation of h-NGF Secreting Fibroblasts

For NGF delivery to aged subjects, monkeys received intraparenchymal grafts of autologous fibroblasts genetically modified to produce and secrete human NGF, as previously described. Briefly, autologous fibroblasts obtained from skin biopsies were genetically modified in vitro to produce and secrete the active, β-portion of human NGF. Transduction procedures were carried out using replication-incompetent retroviral vectors derived from Moloney murine leukemia virus (MLV). Transduced cells were selected by growth in the neomycin analog G418. Production of biologically active NGF was verified by induction of neurite outgrowth from PC12 cells as described; production of NGF mRNA was determined by Northern blot; and amounts of NGF produced from cells were assayed by NGF ELISA specific for human NGF and sensitive to 5 pg/ml. Optimal NGF-producing bulk clones were amplified to numbers sufficient for in vivo grafting by serial passaging. Cells were harvested by gentle trypsinization for in vivo grafting.

EXAMPLE III

Intraparenchymal Delivery of Fibroblasts Genetically Modified to Produce h-NGF Monkeys underwent pre-operative MRI scans (see, Tuszynski, et al., Gene Therapy, 3:305–314, 1996) to visualize basal forebrain target grafting regions (see, Mesulam et al., J. Comp. Neurol., 214:170–197, 1983). After generating stereotaxic grafting coordinates from MRI scans, each monkey received intraparenchymal grafts of autologous NGF-secreting fibroblasts.

Stereotactic coordinates for surgery were generated from magnetic resonance images (MR) of the brain of each subject. The rostral and caudal boundaries of Ch4 were identified on each subject's MR scan, making reference to primate histological brain sections and to standard primate brain atlases. The total rostral-caudal distance of Ch4 was measured on the MR scan, and five graft injection sites were chosen that were equally distributed over this rostral-caudal distance.

The sites for desired ventral-dorsal (VD) and medial-lateral (ML) injections were chosen such that cell grafts were deposited just dorsal to the desired target at each coordinate (within 500 um), and exactly centered in the mediolateral (ML) plane at the maximal density of cholinergic neuronal somata (estimated by review of histological sections at the corresponding AP level). Thus, five grafts were deposited on each side of the Ch4 region per subject, or ten total grafts per subject. Real-time coordinates for in vivo injections were calculated from calibration scales on the MR image. Subjects underwent surgical grafting in the same stereotaxic apparatus that MR scans were performed in.

To place the grafts, animals were placed into a primate stereotaxic apparatus and a midline scalp incision was used to expose the skull. The AP and ML stereotaxic coordinates for the BFC system were used to define the margins of the craniotomy site. Following craniotomy, a ML zero reference point was obtained by measuring the midpoint of the superior sagittal sinus. The dura was incised and reflected to expose the pial surface. The pial surface at each injection site was used as a VD zero reference point for that injection site.

Using the zero reference points obtained in the AP, ML, and VD planes and the stereotaxic injection coordinates calculated from that animal's MR scan, 5 ul of cells were injected into each of 5 sites over the rostral-caudal extent of the Ch4 targeted region bilaterally (10 grafts total per animal) using 25-gauge Hamilton syringe. Grafts were generally targeted to a position slightly dorsal to but within 500 um of Ch4 nuclei. The injection rate was controlled at 5 ul/min. Cells were injected at a concentration of $1.0\times10^5$ cells/ul (for a total of 10 million grafted cells per animal), a concentration that optimally maintains cells in suspension without clumping but sufficiently concentrated to maximize number of surviving cells in vivo. Monkeys survived for three months before sacrifice.

Some control aged subjects received intraparenchymal grafts as noted above. These grafted cells consisted either of autologous fibroblasts transduced to express the reporter gene β-galactosidase (n=6 monkeys). β-gal production was assessed in vitro using a specific anti-β-gal antibody. Cells were grafted into intraparenchymal sites in numbers identical to those described above for NGF graft recipients.

For all surgical procedures, primates were preanesthetized with 25 mg/kg ketamine IM. They were then anesthetized with isoflurane administered by endotracheal intubation. Post-operatively animals were closely monitored, and received supportive care and appropriate analgesics when indicated. Animals were placed in the same primate stereotaxic apparatus (Crist Instruments) that was used to perform MRI scans. A midline scalp incision exposed the skull. A 2.5×5 cm sagittally oriented craniotomy was performed on each side of the hemicranium, and the dura was incised and reflected to expose sites for stereotaxically guided cell injections. Ten ul of cells were injected into each site through a 25 ga. Hamilton syringe at a rate of 1 ul/minute. Postoperatively, all experimental subjects were observed closely for signs of discomfort or toxicity. After a three-month survival period, animals were perfused transcardially for one hour with a 4% solution of paraformaldehyde in 0.1M phosphate buffer followed by 5% sucrose solution in the same buffer for 20 minutes. The brain was stereotaxically blocked in the coronal plane.

EXAMPLE IV

Reversal of Spontaneous Age-Related Loss of p75 Expression in Basal Forebrain Ch4 Neurons In AD brains, NGF accumulates in regions of basal forebrain cholinergic neurons and is decreased in the basal forebrain, leading to the hypothesis that insufficient retrograde transport of NGF promotes the degeneration of basal forebrain cholinergic neurons observed in AD. In humans, basal forebrain cholinergic neuron dysfunction has been closely linked with age-related cognitive and memory impairment.

In the mammalian brain, it is believed that the p75 receptor collaborates with the TrkA receptor to form high-affinity binding sites for NGF. Although activation of TrkA is sufficient for NGF to rescue axotomized cholinergic neurons, disruption of NGF binding to p75 reduces NGF binding to TrkA. Hence, co-expression of the two receptors can lead to greater responsiveness to NGF. Conversely, loss of expression may lead to decreased responsiveness to NGF. Expression of both p75 and TrkA is regulated by NGF, so that a loss of NGF signalling further reduces the amount of both p75 and TrkA. Combined with a loss of expression of TrkA in AD brains, leading to reduced amounts of TrkA protein in both the basal forebrain and the cortex, decreased p75 expression may contribute to a decline in retrograde NGF signalling. Thus, p75 expression is a marker for NGF binding, basal forebrain cholinergic neuron dysfunction and cognitive impairment.

To determine the effect of the method of the invention on p75 expression in treated primate brains, monkeys were treated as described in Example III. Each subject was then deeply anesthetized with ketamine and nembutal and perfused transcardially for 1 hour with a 4% solution of paraformaldehyde in 0.1M phosphate buffer, followed by 5% sucrose solution in the same buffer for 20 min. The brains were then stereotaxically blocked in the coronal plane to obtain a single block containing the full AP extent of Ch4.

Coronal sections were cut on a freezing microtome set at 40 um. Every sixth section was processed for p75 immunoreactivity. Briefly, sections were washed thoroughly in Tris-buffered saline (TBS) and endogenous peroxidases were quenched by incubating in a 0.6% hydrogen peroxide solution. Sections were rinsed in TBS and then blocked using 5% donkey serum with 0.5% Triton X-100 in TBS (TBS++). Incubation in primary antibody (monoclonal diluted 1:100 in TBS++) occurred for 24 hours at room temperature. Sections were rinsed in TBS++, incubated in secondary antibody (biotinylated donkey-anti-mouse diluted 1:500 in TBS++) for 1 hour, rinsed again in TBS++, and then incubated for 90 minutes using a Vector ABC kit. p75-labeled neurons were then visualized using diaminobenzidine (DAB) as a chromogen. Sections were then mounted and coverslipped.

75-labeled neurons were quantified in Ch4i neurons using stereological procedures. Ch4i was targeted in this study since this region is the principal site of origin of cholinergic projections to cortical regions that modulate memory. Thus, for the purposes of stereology, it was necessary to first identify the Ch4i region of the brain.

Ch4 can be divided topographically into three subdivisions, the anterior (Ch4a), intermediate (Ch4i), and posterior (Ch4p). The anterior subdivision is further divided into medial (Ch4am) and lateral (Ch4al) sectors, which are divided by a vascular structure or rarefication in the density of neurons. However, as Ch4a travels in the posterior direction toward Ch4i, the division between Ch4am and Ch4al becomes less distinct and in some disappears. In this region the ansa peduncularis, the characteristic structure of Ch4i, begins to make its appearance. The ansa peduncularis divides Ch4i into ventral (Ch4iv) and dorsal (Ch4id) components. There is typically also a portion of the anterior commissure present over the lateral portion of Ch4id at this level that serves as the anterior boundary of Ch4i. At the posterior boundary of Ch4i, Ch4iv and Ch4id merge into a single nucleus embedded in the intersection of the globus pallidus, putamen, and optic tract.

Stereological counts were performed on every sixth section through the entire extent of Ch4i. The NeuroZoom™ stereology computer program running on an Apple Macintosh™ PowerPC™ and connected to a Javelin™ video camera mounted on an Olympus Vanox™ AHBT-3 microscope was used to conduct stereology by the well-known West optical dissector method. Briefly, the region of interest (Ch4i) was outlined in NeuroZoom™ using a 1X objective. Specific stereology parameters were then set in NeuroZoom™:

Fraction (percent of area): 5%
Counting frame size: x=66.46 um, y=53.73 um
Section thickness: 40 um These parameters were adjusted to minimize the coefficient of error of the estimate (CE(P)) while maximizing the efficiency of sampling.

The NeuroZoom™ program controlled movement from one counting frame to the next by moving a Ludl motorized stage mounted on the microscope. Ch4i neurons were counted using a 60X high numerical aperture (1.40) oil objective. Cells were marked to be included in the count if they met the following criteria: 1) they were p75-labeled; 2) the soma was within the counting frame (or touching the inclusion boundary) but did not touch the exclusion boundary; 3) a clearly visible nucleus was present; and 4) the nucleus was best in focus within the inclusion volume (i. e., the top 12.5% and bottom 12.5% were excluded, and the nucleus was not in focus in either of these exclusion volumes). Multiple group comparisons were made by analysis of variance (ANOVA) with post-hoc analysis using Fisher's least squares difference.

The number of p75-labeled Ch4i neurons was compared between four groups of rhesus monkeys, two of which were unoperated and two of which received intraparenchymal grafts of genetically-modified fibroblasts. Young monkeys (mean age=9.375±1.058) constituted one of the unoperated groups, while aged monkeys (mean age=25.139±2.455) comprised the other unoperated group. Of the two aged groups which received grafts to the basal forebrain, one (mean age=22.639±0.463) received grafts of cells modified to produce and secrete NGF, and the other (mean age= 23.321±0.927) received grafts of cells modified to produce and secrete β-gal.

There were significantly fewer p75-labeled neurons in Ch4i from unoperated aged monkeys than from unoperated young monkeys (p<0.01). The mean number of p75-labeled Ch4i neurons from NGF-grafted aged monkeys was significantly greater than from control-grafted aged monkeys (p<0.04). Further, there number of p75-labeled Ch4i neurons in NGF-grafted aged monkeys did not differ from numbers in unoperated young monkey brains (p=0.1288).

These results demonstrate that there is spontaneous loss of expression of the low-affinity neurotrophin receptor (p75) in cholinergic neurons in the basal forebrain, and that re-expression of p75 can be induced by intraparenchmal delivery of NGF.

EXAMPLE V

Histology Confirming In Vivo Uptake of Donor Cells Expression of NGF and Lack of β-Amyloid Induction Sections of brain tissue after humane sacrifice of the test animals were cut at 40 um intervals on a freezing microtome. Every sixth section was processed for Nissl stain or hematoxylin and eosin. Immunocytochemical labeling against β-amyloid was performed using an amyloid-specific monoclonal antibody (anti-βA4). Sections lacking primary antibody were processed to verify specificity of labeling. A representative section per subject was quantified from each of the following regions: temporal, frontal, cingulate, insular, parietal and occipital cortices; amygdala and hippocampus; and the intermediate division of the Ch4 region (Nucleus Basalis of Meynert). Sampled sections from each subject were closely matched in region and size. The total number of amyloid plaques per region was quantified and recorded. Observers were blinded to the identity of the tissue being quantified.

All grafted subjects showed surviving cell grafts within 500 um of each grafting site. There was no qualitative difference in fibroblast morphology and overall graft size between NGF- and control-graft recipients. Grafts were most frequently located adjacent to the intermediate division of the Ch4 region of the basal forebrain, but in all cases included at least one graft located within the anterior and posterior divisions of the Ch4 region.

No amyloid plaques at all were detected in adult, non-aged primate tissue. In contrast, control aged monkeys showed a significant increase in amyloid immunolabeling in the frontal, temporal insular and cingulate cortices and amygdala, and extremely small increases in the parietal cortex and hippocampus relative to non-aged monkeys. No plaques at all were present in the cholinergic basal forebrain in any group.

In aged control animals, plaques typically showed a dense central core and a less dense surrounding halo of immunreactive deposition product, an appearance typical of "mature" plaques observed in AD. This immunolabeling pattern is consistent with previous reports in aged primate brain. However, no increase in amyloid labeling was observed in the aged, NGF-grafted brains, indicating that three months of intraparenchymal NGF delivery does not increase β-amyloid plaque deposition in the aged primate brain. Thus, the benefits of NGF grafting in the brains of primates exhibiting AD symptoms can be acheived without risk of stimulating amyloid deposition in response to the graft trauma.

Initially, group differences were statistically determined by analysis of variance, with post-hoc analysis utilizing Fisher's least square difference. However, since non-aged adult monkeys showed no amyloid plaques, comparisons between NGF-treated and control aged monkeys were made using unpaired two-way student's t-test.

The invention claimed is:

1. A method for intraparenchymal delivery of a therapeutic nerve growth factor to cells in the primate brain to treat basal forebrain cholinergic neuron dysfunction in Alzheimer's Disease, the method comprising grafting donor cells into multiple grafting sites in the cholinergic basal forebrain of a human or non-human primate, wherein the donor cells are genetically modified by insertion therein of at least one transgene encoding a nerve growth factor; and wherein the donor cells are grafted into each grafting site in a pharmaceutically acceptable fluid composition having a concentration of donor cells of at least $1 \times 10^5$ cells/$\mu$l fluid; and wherein the donor cells are delivered to each grafting site in a dosage of between 6 and 20 $\mu$l; and wherein further each grafting site is no more than about 500 $\mu$m from a defective, diseased or damaged brain cell and no more than about 5 mm from any other grafting site.

2. The method according to claim 1 wherein the mammal is a human and the transgene encodes a human neurotrophin.

3. The method according to claim 2 wherein the transgene encodes nerve growth factor (NGF)β.

4. The method according to claim 2 wherein the transgene encodes neurotrophin 3 (NT3).

5. The method according to claim 1 wherein the grafting sites are all within the Ch4region of the cholinergic basal forebrain.

6. The method according to claim 1 wherein the transgene is carried by a retroviral vector.

7. The method according to claim 6 wherein the donor cell composition is delivered to each grafting site in a dosage of between 2 and 20 $\mu$l.

8. The method according to claim 7 wherein the donor cell composition is delivered to each grafting site at a rate of about 0.2 µl cell suspension/minute to about 4 µl cell suspension/minute.

9. The method according to claim 7 wherein the donor cell composition is delivered to each grafting site over a period of 5 to 10 minutes.

10. The method according to claim 1 wherein the donor cells are primary fibroblasts.

11. The method according to claim 10 wherein the fibroblasts are primate fibroblasts.

12. The method according to claim 11 wherein the fibroblasts are human fibroblasts.

* * * * *

UNITED STATES PATENT AND TRADEMARK OFFICE
CERTIFICATE OF CORRECTION

PATENT NO.   : 6,451,306 B1
DATED        : September 17, 2002
INVENTOR(S)  : Mark H. Tuszynski and Fred H. Gage It is certified that error appears in the above-identified patent and that said Letters Patent is hereby corrected as shown below:

<u>Column 16,</u>
Line 65, after "between", delete "2" and substitute -- 10 --

Signed and Sealed this

First Day of April, 2003

JAMES E. ROGAN
*Director of the United States Patent and Trademark Office*